United States Patent
Kiselev et al.

(10) Patent No.: US 8,231,871 B2
(45) Date of Patent: Jul. 31, 2012

(54) PERORALLY ADMINISTRABLE ANTIMICROBIAL COMPOSITION

(76) Inventors: Nikolai Alexandrovich Kiselev, Moscow (RU); Dmitry Sergeevich Chicherin, Moskovskaya obl. (RU)

(*) Notice: Subject to any disclaimer, the term of this patent is extended or adjusted under 35 U.S.C. 154(b) by 424 days.

(21) Appl. No.: 11/661,472

(22) PCT Filed: Aug. 25, 2005

(86) PCT No.: PCT/RU2005/000434
§ 371 (c)(1), (2), (4) Date: Feb. 26, 2007

(87) PCT Pub. No.: WO2006/025767
PCT Pub. Date: Mar. 9, 2006

(65) Prior Publication Data
US 2007/0254023 A1    Nov. 1, 2007

(30) Foreign Application Priority Data
Aug. 30, 2004  (RU) ................ 2004126203

(51) Int. Cl.
*A61K 31/43*  (2006.01)
*A61K 31/545*  (2006.01)
*A61K 31/65*  (2006.01)

(52) U.S. Cl. ........ 424/114; 424/489; 424/451; 514/152; 514/192; 514/200

(58) Field of Classification Search .......... None
See application file for complete search history.

(56) References Cited

U.S. PATENT DOCUMENTS

| 4,963,141 A | * | 10/1990 | Eckenhoff | 604/892.1 |
| 5,415,695 A | * | 5/1995 | Weterings et al. | 127/58 |
| 6,221,853 B1 | * | 4/2001 | Salsarulo et al. | 514/53 |
| 6,972,132 B1 | * | 12/2005 | Kudo et al. | 424/461 |
| 2004/0247675 A1 | * | 12/2004 | Gruber | 424/471 |

FOREIGN PATENT DOCUMENTS
RU  2131260 C1 * 6/1999
WO  WO 9959413 A1 * 11/1999

OTHER PUBLICATIONS

Masataka Katsuma et al. Studies on lactulose formulations for colon-specific drug delivery, International Journal of Pharmaceutics 249 (2002) 33-/43.*
David Teller et al. Antibiotics 2005—An Update, Dec. 22, 2004.*
Mark Battle et al, "Probiotics and antibiotic associated diarrhea", BMJ, vol. 325, Oct. 19, 2002.*
S. Shah et al., Gastric acid suppression does not promote clostridial diarrhea in elderly, Q J Med 2000; 93:175-181.*

* cited by examiner

*Primary Examiner* — Michael G Hartley
*Assistant Examiner* — Nabila Ebrahim
(74) *Attorney, Agent, or Firm* — Defillo & Associates, Inc; Evelyn A. Defillo

(57) ABSTRACT

The invention relates to medicine and the chemical and pharmaceutical industry, in particular to antibiotic preparative forms. The inventive antimicrobial composition contains antibiotic selected from a group of lincosamides, broad-spectrum penicillins, cephalosporins, macrolides, tetracyclines, and lactulose at the active component ratio of 1:1-1:100. The mean particle size of lactulose ranges from 100 nm to 200 μm. Said composition is embeddable in a solid state and in the form of a syrup or a suspension. When applicable, pharmaceutically acceptable excipients are added into the composition in such a way that it takes a form acceptable for peroral administration.

2 Claims, No Drawings

PERORALLY ADMINISTRABLE ANTIMICROBIAL COMPOSITION

CROSS REFERENCE TO RELATED APPLICATION

This application is a national stage of PCT/RU2005/000434 filed Aug. 25, 2005 and based upon Russian Application No. RU2004126203 filed Aug. 30, 2004, under the International Convention.

TECHNICAL FIELD OF THE INVENTION AND PRIOR ART

The invention relates to medicine and chemical and pharmaceutical industry, in particular to antibiotic preparative forms.

It is contagious diseases that have always posed the maximum threat to the health of the mankind.

The discovery and introduction of antimicrobial medicines to the clinical practice was the greatest milestone in the history of the human fight against contagious diseases. Due to the high efficacy related to the treatment of contagious diseases, antibiotics were first named "wonder drugs." For a long time no one paid due attention to adverse effects of antibiotics. At the same time, nobody denied their presence since the results of using antibiotics were so impressive. However, the problem of adverse effects of antibiotics acquires a global scale and needs to be solved now.

The fact that patients treated with antibiotics develop antibiotic-associated diarrheas and colitis is one of the urgent problems of clinical medicine.

The lack of awareness among physicians about the problem results in the fact that diarrheas in patients receiving an antibacterial therapy are most frequently diagnosed as the "bowel dysbacteriosis", which can be just a background for the bowel colonization with potentially pathogenic microflora.

At present *C. difficile* infection is considered as one of the most important etiological factors for the development of diarrheas and colitis. However, they can be associated with other bacteria as well, e.g. *Salmonella* spp., *Clostridium perfringens* type A, *Staphylococcus aureus* and perhaps *Candida* fungi.

Such drugs as metronidazole and vancomycin, which are similar by their clinical efficacy, as well as some other less efficient antibiotics are the key antibacterial drugs applied in case of *C. difficile* infection. Unfortunately, none of the etiotropic regimens of *C. difficile* treatment being in current use can guarantee the bowel sanation against *Clostridium* spores. In this connection, relapses are quite probable.

Since the abnormal composition of the bowel endogenous microflora is a key factor for adverse effects related to the use of antibiotics, recommendations to use biopreparations, in particular, Saccharomyces boulardii non-pathogenic yeast, seem to be very promising. However, their application fails to ensure the non-occurrence of relapses as well.

In the clinical practice, antibiotics are used as different drug forms such as pills, capsules, parenteral solutions, suppositories, syrups, etc.

Lactose and other sugars as well as sugar-based alcohol, cellulose derivatives, starch and organic food acids or their salts enabling to improve the drug organoleptic properties are used as traditional carriers (Russian Patents No. 2202340-C1, published Apr. 20, 2003; No. 2085190-C1, published Jul. 27, 1997; No. 1805953-A3, published Mar. 30, 1993).

Peroral forms of antibiotics as gel compositions comprising polyethylene oxide and hydrophilous base are known (Russian Patents No. 2220715-C2, published Apr. 10, 2004). The composition is intended for stabilization of drugs at their storage but fails to solve the problem of the adverse effect of antibiotics.

An antimicrobial combined drug named "tetracycline with nystatin" containing tetracycline—a bacteriostatic pluripotential antibiotic drug—and nystatin—an antifungal drug—are known (see, for example, M. D. Mashkovsky, Lekarstvennye sredstva, Moscow, Meditsina, vol. 2., p. 255).

Nystatin added to drug forms of antibiotics prevents the development of candidiasises but fails to prevent the development of other adverse effects they have.

SUMMARY OF THE INVENTION

The goal of the invention is to obtain an antibiotic drug in a form acceptable for peroral administration, being highly active and stable during storage and preventing adverse effects.

The goal is achieved in the form of a new antimicrobial composition comprising an antibiotic selected from the group consisting of lincosamides (e.g. clindamycin), broad-spectrum penicillins (e.g. ampicillin and amoxicillin), cephalosporins (e.g. cefalexin and cefixime), tetracyclines (e.g. doxycycline and tetracycline), macrolides (e.g. erythromycin), and lactulose at the ratio of 1:(1-100) while the mean particle size of lactulose ranges from 100 nm to 200 µm. When applicable, pharmaceutically acceptable excipients are added into the composition in such a way that it takes a form acceptable for peroral administration.

The peroral form can be syrup, suspension, powder, pill, capsule, granules.

Lactulose is an unadsorbed syntetic disaccharide (4-0-β-D-galactopyranosyl-D-fructose) being an optical isomer of lactose. Lactulose in its natural form can be found only in breast milk and just in small amounts. It is remarkable, first of all, for being a powerful stimulator of vital functions of the human symbiotic microflora and, secondly, it is not absorbed into blood in the stomach and bowels (the respective ferments are absent) but enters the sites inhibited by lactobacilli and bifidobacteria practically in full where they absorb it by 90-100% and produce the lactic and acetic acids. At the same time, the reaction of the large intestine medium is changed from alkalescent being optimal for putrid microflora to the acid one. Thus, in spite of the fact that the lactulose molecule comprises digestible galactose and fructose residues, the human organism fails to obtain carbohydrates. Instead of them, it obtains products of their microbial fermentation comprising mainly the lactic, acetic, propionic and butyric acids. In an acid medium, products of metabolism of putrid microflora (mainly ammonia) are dissociated into ions, which are not absorbed by the mucous tunic of the colon. Due to this, intoxication of the body is prevented. The pH reduction in the colon contributes to the cessation of decomposition of proteins.

In 1957, F. Petuely discovered the bifidogenic activity of lactulose and named lactulose as "bifidogenic agent". Being an ideal substrate for bifidobacterias and lactate-producing germs, lactulose modifies the microflora composition by increasing the number of bifidobacterias and lactobacilles. Moreover, a substantial reduction in the number of Fusobacterias, Clostridiums and Bacteroides being a measure of potentially pathogenic microbes was observed. Lactulose decontaminates chronic Salmonella carriers.

As it is known, by selecting a balanced combination of drugs as well as accessory substances—excipients—in a number of cases it is possible to improve their therapeutic activity, change their pharmakocinetic and pharmacodynamic features, and reduce their toxicity. However, such combinations may cause an opposite effect as well. An unreasonable combination leads to the reduction, distortion or absolute loss of the drug remedial effect. This may happen mainly due to the phenomena of complex formation, adsorption or decomposition that can abruptly change the rate and completeness of the adsorption of substances.

In addition to the above-mentioned adverse effects inherent to antibiotic drugs, their instability represents a problem as well.

DETAILED DESCRIPTION OF PREFERRED EMBODIMENT OF THE INVENTION

It turned out rather unexpectedly that when the present combinations of antibiotics and lactulose are used at a certain proportion and if the powder of the latter is pre-crushed down to the size of 100 nm-200 µm, it is possible to obtain stable forms. At the same time, the abnormal flora of the bowel is prevented and/or normalized and accordingly antibiotic-associated disorders are prevented.

The adsorbing properties of lactulose were expected to slow down or decrease the efficacy of antibiotics. However, the studies showed that the substance in the present combination proves to be highly efficient.

Antibiotics as well as most drug substances are not capable of direct pelletization and require introduction of accessory agents. At the same time, the damp granulation technology often results in the decomposition of drugs and reduction of their activity. Lactulose makes it possible to exclude this stage from the process of pelletization. Moreover, no large amounts of accessory substances are needed because lactulose is an excellent excipient itself.

Poor organoleptic characteristics are another problem related to the production of preparative forms of antibiotics. The addition of lactulose enables to improve the taste qualities of the compositions.

Antibiotics form a part of the compositions in generally accepted and therapeutically efficient doses.

If needed, different excipients can be added, e.g. aromatizers, flavoring substances, colorants, acceptable organic acids, starch and its derivatives, PVP, microcrystalline cellulose or cellulose derivatives, mannitol, stearates, talc, etc.

The feasibility of the invention is illustrated by the following examples:

Example 1

Syrup:
Cefalexin 1.5 g
Lactulose 30 g
Lactose 10 g
Galactose 30 g
Citric acid 1 g
Strawberry aromatizer 1 g
Water up to 100 ml

Example 2

Pills 0.5 g:
Ampicillin 50 mg
Lactulose (100 µm) 250 mg
Microcrystalline cellulose 95 mg
Starch 100 mg
Magnesium stearate 5 mg

Example 3

Film-Coated Pills:
Core:
Tetracycline 100 mg
Lactulose (200 µm) 100 mg
Starch 44 mg
Talc 2 mg
Magnesium stearate 4 mg
The film comprises an oxypropylmethylcellulose, PEG 6000 and titanium dioxide at the ratio of 6.5:1:1.

Example 4

Powder-Containing Gelatin Capsules:
Clindamycin 150 mg
Lactulose (100 nm) 450 mg

Example 5

Peroral Suspension:
Sodium salt of phenoxymethylpenicillin 1.2 g
Lactulose (200 µm) 3.6 g
Water up to 100 ml

Example 6

Gelatin Capsules:
Sodium salt of oxacillin 250 mg
Lactulose (100 µm) 250 mg

Example 7

Granules in Sachets:
Cefaclor 125 mg
Lactulose (100 µm) 12.5 g

Example 8

Pills:
Erythromycin 100 mg
Starch 37.5 mg
Microcrystalline cellulose 10 mg
Lactulose (100 µm) 100 mg
Calcium stearate 2.5 mg

Example 9

Comparative Experimental Trials of the Effect of Peroral Administration of Antibiotics and an Antibacterial Composition Comprising an Antibiotic and Lactulose on Gut Organisms and Liver Condition in CBA Mice Models of experimental pathology caused by peroral administration of ampicillin and tetracycline in large doses were used.

A ten-day course of peroral administration of ampicillin in the dose of 350 mg/kg reduced the content of bifidobacteria in the alimentary tract of mice to a certain degree.

When the aforesaid antimicrobial composition comprising ampicillin and lactulose according to Example 2 was used, the evident bifidogenic effect (by 4-5 lg higher than in intact animals) was observed.

Ampicillin also substantially inhibited the growth of lactobacilli by 100 times). On the contrary, administration of the composition according to Example 2 prevented the decrease in the number of lactobacteria. Their number was higher than that in the mice receiving only one antibiotic by 3 lg, and was slightly higher than in the control group.

A ten-day course of peroral administration of tetracycline in the dose of 750 mg/kg reduced the contents of bifidobacteria in the large intestine.

The introduction of the antimicrobial composition containing tetracycline and lactulose according to Example 3 prevented the inhibition of bifidoflora as well as the number of bifidobacteria was even higher than at the baseline (by 2 lg).

A ten-day course of peroral administration of the antimicrobial compositions according to Example 2 and Example 3 normalized the mucous coat morphology of both small and large intestines, and prevented toxic drug-induced hepatitis.

Similar results were obtained during a study of compositions containing clindamycin and lactulose according to Example 4, erythromycin and lactulose according to Example 8, and cefalexin and lactulose according to Example 1.

Example 10

Experimental Study of the Biological Activity

The antimicrobial activity was studied by the method of serial dilutions of Staphylococcus aureus daily agar test culture. The broth in the volume of 1 ml each was poured into 10 sterile tubes, 1 ml of the suspension according to Example 5 was added, mixed, then 1 ml was transferred into the second tube, etc. Dilutions with the commercial suspensions were prepared by the same method. The suspended microbial mixture was brought into all tubes with the antibiotic and control tubes, then tubes were stored in the thermostat at 37° C. for 24 hours, and then tubes with the evident inhibition of the microbial growth were selected. The study showed that similar results were obtained both for present and known mixtures: the activity amounted to 0.1-0.2 mkg/ml.

Thus, the addition of lactulose does not reduce the antibiotic activity.

Example 11

The therapeutic effect of the drugs was also studied in a group of patients with acute enteric infections.

Peroral doses of ampicillin and nystatin were administered to the patients based on the generally accepted scheme. Their condition improved and their stool became normal on the 9$^{th}$-10$^{th}$ day of treatment. The drug according to Example 2 was prescribed for another group of patients. Their condition improved on the 3$^{rd}$ day of treatment and their stool became normal on the 4th-5$^{th}$ day of treatment.

The microbiological study of the bowel microflora showed the presence of *Escherichia* (Lac$^-$) in the first study group on the 10$^{th}$ day of treatment; patients of the second group demonstrated a negative results for the potentially pathogenic flora in the liquid nutrient medium (beef extract broth) on the 5$^{th}$ day of the study. This was used for experiments.

Example 12

A Study of the Drug Stability

The drug stability was studied on the basis of accelerated ageing models at the temperature of 37° C. Samples were taken every 10 days.

The example when lactulose was not crushed down was used as Control 1. The lactulose-free drug was used as Control 2. The stability was assessed based on the change in the minimum inhibitory activity related to the Staphylococcus aureus standard strain.

The results are given in Table 1.

TABLE 1

| Test specimen | Experimental shelf-life, days | Equivalent shelf-life, years | Minimum inhibitory activity (mkg/ml) | Identity |
|---|---|---|---|---|
| Composition according to Example 6 | 10 | 0.5 | 0.1-0.2 | Match |
|  | 20 | 1 | 0.1-0.2 | Match |
|  | 30 | 1.5 | 0.3-0.4 | Match |
|  | 40 | 2 | 0.4-0.5 | Match |
|  | 50 | 2.5 | 0.7-0.8 | Match |
|  | 60 | 3 | 1.0-1.2 | Match |
| Control 1(6) | 10 | 0.5 | 0.1-0.2 | Match |
|  | 20 | 1 | 0.2-0.3 | Match |
|  | 30 | 1.5 | 0.3-0.4 | Match |
|  | 40 | 2 | 0.6-0.8 | Match |
|  | 50 | 2.5 | 1.0-1.2 | Match |
|  | 60 | 3 | 1.5-2.0 | Match |
| Control 2(6) | 10 | 0.5 | 0.1-0.2 | Match |
|  | 20 | 1 | 0.4-0.6 | Match |
|  | 30 | 1.5 | 0.8-1.0 | Match |
|  | 40 | 2 | 2.2-2.4 | Match |
|  | 50 | 2.5 | 3.6-3.8 | Match |
|  | 60 | 3 | 4.5-5.0 | — |
| Composition according to Example 8 | 10 | 0.5 | <0.02 | Match |
|  | 20 | 1 | 0.02-0.03 | Match |
|  | 30 | 1.5 | 0.04-0.08 | Match |
|  | 40 | 2 | 0.08-0.15 | Match |
|  | 50 | 2.5 | 0.2-0.3 | Match |
|  | 60 | 3 | 0.3-0.6 | Match |
| Control 1(8) | 10 | 0.5 | <0.02 | Match |
|  | 20 | 1 | 0.04-0.08 | Match |
|  | 30 | 1.5 | 0.1-0.15 | Match |
|  | 40 | 2 | 0.2-0.4 | Match |
|  | 50 | 2.5 | 1.0-1.4 | Match |
|  | 60 | 3 | 2.0-2.6 | Match |
| Control 2(8) (carboxymethyl cellulose was used instead of lactulose) | 10 | 0.5 | <0.02 | Match |
|  | 20 | 1 | 0.08-0.1 | Match |
|  | 30 | 1.5 | 0.6-1.0 | Match |
|  | 40 | 2 | 3.2-5.0 | Match |
|  | 50 | 2.5 | 7.0-7.5 | Match |
|  | 60 | 3 | >200 | Match |

Thus, the suggested peroral antibacterial composition prevent adverse effects of antibiotic drugs.

The compositions for peroral administration according to present invention are stable and efficient forms having practically any adverse effects. The pills, powders and capsules as well as syrup containing the present pharmaceutical composition can be recommended for clinical application on a broad scale.

The invention claimed is:

1. An antimicrobial composition for peroral administration having active ingredients consisting of:
   a) a broad-spectrum antibiotic selected from the group including penicillins, cephalosporins, tetracyclines, lincosamides, macrolides; and
   b) lactulose;
   wherein the broad spectrum antibiotic and the lactulose are present at a ratio of 1:1-1:30;
   wherein the lactulose has a mean particle size between 100 nm to 200 μm;
   wherein the broad spectrum antibiotic and lactulose are present in the same composition; and
   wherein the composition is made in the form of a pill, a powder, a capsule, a granule, a syrup, or a suspension.

2. An antimicrobial composition for peroral administration having active ingredients consisting of:
   a) a broad-spectrum antibiotic selected from the group including penicillins, cephalosporins, tetracyclines, lincosamides, macrolides;
   b) lactulose; and
   c) pharmaceutical acceptable excipients;
   wherein the broad-spectrum antibiotic and the lactulose are present at a ratio of 1:1-1:30,
   wherein the lactulose has a mean particle size between 100 nm to 200 μm; and
   wherein the broad-spectrum antibiotic and lactulose are present in the same composition.

* * * * *